(12) United States Patent
Adams (10) Patent No.: US 10,532,136 B2
(45) Date of Patent: Jan. 14, 2020

(54) NOISE-SUPPRESSING, SUCTION PROBE APPARATUS AND METHOD

(71) Applicant: Jason P. Adams, Farmington, NM (US)

(72) Inventor: Jason P. Adams, Farmington, NM (US)

( * ) Notice: Subject to any disclaimer, the term of this patent is extended or adjusted under 35 U.S.C. 154(b) by 543 days.

(21) Appl. No.: 13/941,653

(22) Filed: Jul. 15, 2013

(65) Prior Publication Data

US 2014/0316357 A1    Oct. 23, 2014

Related U.S. Application Data

(63) Continuation of application No. 29/452,746, filed on Apr. 22, 2013, now Pat. No. Des. 794,176, and a continuation of application No. 29/452,752, filed on Apr. 22, 2013, now Pat. No. Des. 713,027.

(51) Int. Cl.
  *A61M 1/00* (2006.01)
  *A61M 3/00* (2006.01)
  *A61M 5/00* (2006.01)

(52) U.S. Cl.
  CPC ............. *A61M 1/0031* (2013.01); *A61M 1/00* (2013.01); *A61M 1/0047* (2013.01); *A61M 3/00* (2013.01); *A61M 5/00* (2013.01); *A61M 2202/0014* (2013.01); *A61M 2205/42* (2013.01); *A61M 2207/00* (2013.01)

(58) Field of Classification Search
  CPC ...... A61M 25/00; A61M 25/01; A61M 25/06; A61M 25/10; A61M 39/00; A61M 39/10; A61M 39/12; A61M 39/14; A61M 39/20; A61M 1/00; A61M 3/00; A61M 5/00; A61M 5/142; A61M 5/168; A61M 5/34; A61M 35/00; A61M 1/0031; A61M 1/0047; A61M 2202/0014; A61M 2205/42; A61M 2207/00; A61F 5/44; A61F 5/451; A61F 5/455
  USPC .......................................................... 604/319
  See application file for complete search history.

(56) References Cited

U.S. PATENT DOCUMENTS

| | | | | |
|---|---|---|---|---|
| 4,049,000 A | * | 9/1977 | Williams | A61M 1/0047 433/95 |
| D247,915 S | | 5/1978 | Lahay | |
| 5,195,952 A | * | 3/1993 | Solnit | A61C 17/043 433/91 |
| 6,565,544 B1 | | 5/2003 | Rainin | |
| 2005/0004520 A1 | * | 1/2005 | Lemoine | A61C 17/043 604/118 |
| 2011/0087169 A1 | * | 4/2011 | Parihar | A61B 17/34 604/167.03 |

OTHER PUBLICATIONS

English translation of JP 11-276594 A to Kawakita et al.*
(Continued)

*Primary Examiner* — Andrew J Mensh
(74) *Attorney, Agent, or Firm* — Pate Baird, PLLC (57) ABSTRACT

A suction tool having a hollow handle and a probe extending from the handle near one end of the handle to define a lumen in fluid communication with the hollow handle and a fitting, formed to extend near the other end of the handle and shaped to receive a vacuum source drawing fluids through the probe, handle, and fitting. The handle also includes an aperture extending at an acute angle with respect to the axis of the handle.

12 Claims, 6 Drawing Sheets

(56) References Cited

OTHER PUBLICATIONS

Ace Surgical Supply Co., Inc., Frazier Metal Suction Tips, http://www.acesurgical.com/suction/suction-tips/suction-tips-ejectors/frazier-metal-suction-tips-10fr-frazier-suction-olive-tip.html, Date Unknown.

* cited by examiner

NOISE-SUPPRESSING, SUCTION PROBE APPARATUS AND METHOD

RELATED APPLICATIONS

This application: is a continuation of co-pending U.S. patent application Ser. No. 29/452,746 filed Apr. 22, 2013; and is a continuation of co-pending U.S. patent application Ser. No. 29/452,752 filed Apr. 22, 2013; both of which are hereby incorporated by reference.

BACKGROUND

Field of the Invention

This invention relates to surgical tools and, more particularly, to novel systems and methods for suction probe structures, manufacture, and use.

Background Art

Surgical procedures depend upon visibility. Accordingly, fluids that collect in interstitial bodily spaces, such as in an abdomen or other areas, require suctioning. Similarly, clearance of collected fluids, either from leakage, incisions, collection, washing, or the like is often required.

To this end, various types of probes or suctioning apparatus have been developed. One such probe is referred to as a suction probe or Frazier tip. A Frazier tip operates to permit air to enter a handle, thus breaking the vacuum or the draw that would otherwise occur at the outermost tip or point of the probe. However, such a passage of air causes an annoying, and interfering, high-pitched, whistling noise.

Theoretically, the opening available in the handle is supposed to provide control. A surgeon or assistant may place a thumb over the opening in order to close a handle to the passage of air. The result is an immediate draw at the tip, the only remaining open location in the probe. Upon release of the thumb over the opening, air is drawn in much more easily than liquid fluids, and the suctioning reduces substantially and may reduce entirely. That is, the tip of the probe is no longer effective, and will not tend to suction, nor to grab at other surfaces in the region. Thus, the probe may be left in place, and simply touched at the aperture periodically in order to perform a suctioning function.

As a result of the annoying, even aggravating, high-pitched whistle, doctors frequently place tape over the aperture in the handle. This renders control of the Frazier tip ineffective. With the aperture sealed at all times, suction never ceases at the tip. Thus, as a practical matter, the Frazier tip operates as a constant-suction device, and fails in its supposed function as a controllable suction device.

Alternatively, the leaving of a Frazier tip with the aperture open causes such a loud, constant, high-pitched whistling that conversation, instructions, and other communication in an operating room are seriously compromised. What is needed is some solution to the currently unacceptable trade off between constant suction or interference with procedures by ongoing noise.

BRIEF SUMMARY OF THE INVENTION

In view of the foregoing, in accordance with the invention as embodied and broadly described herein, a method and apparatus are disclosed in one embodiment of the present invention as including a probe and manufacturing method for reducing the failure and providing a system without the whistling noise, yet still providing controllable suction in a Frazier tip. In certain embodiments, an aperture is molded into a handle of a probe to provide a minimization of acoustic disturbances. Angling the aperture, or the tubular passage from the exterior of the handle down into the interior cavity has been shown effective to eliminate the whistling noise.

Angling the passageway to join the central cavity in the handle at an acute angle reduces sufficiently the disturbance and oscillations that heretofore have been known.

An angle of from about 30 degrees to about 70 degrees appears to serve adequately. An angle of from about 30 degrees to about 60 degrees is preferable, and an angle from about 30 degrees to about 45 degrees is more preferable. Angles less than 30 degrees between the cavity or central passage of the handle, and the axis of the passage from the external aperture or thumb-hole passage work very well. However, such small acute angles are extremely difficult to form, and create other manufacturing problems.

In certain embodiments, a handle for a Frazier tip may be molded in a two-piece mold in a variety of ways. Typically, core-pulls may be required, if the handle is to be manufactured in a single step, or in a single molding step, with no post-molding assembly of the handle. In other embodiments, the two halves of a handle may be each molded separately in a two-piece injection mold, and the handle halves may be glued together subsequently.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 1:
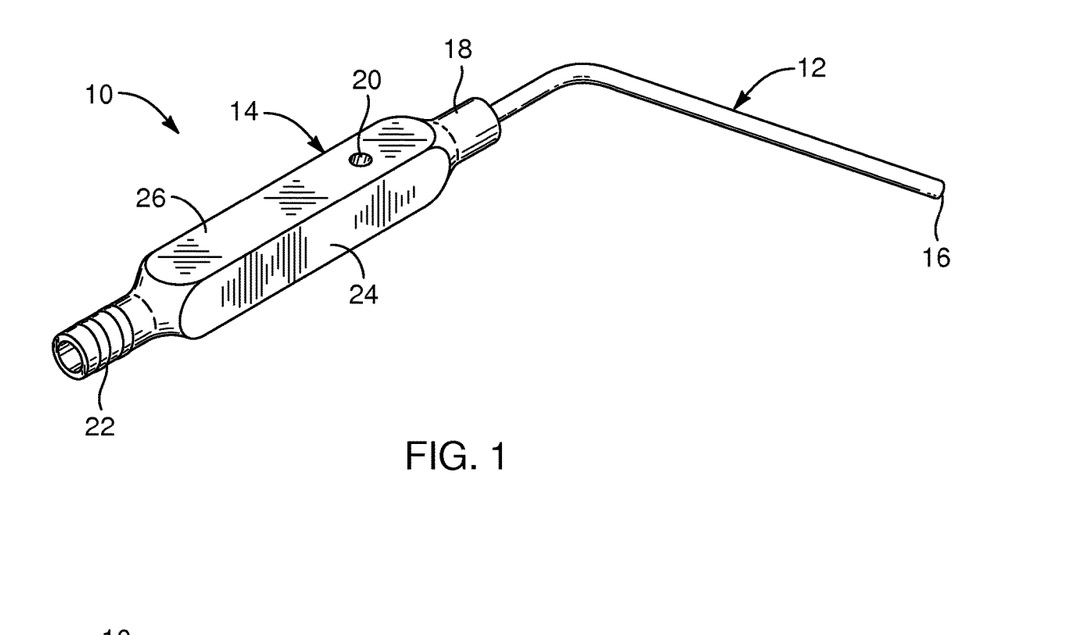
FIG. 1 is a perspective view of one embodiment of an apparatus in accordance with the invention.
Figure 2:
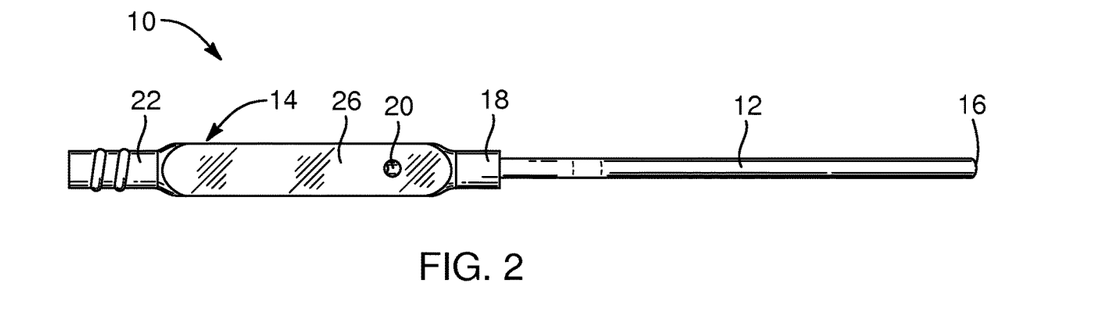
FIG. 2 is a top plan view thereof.
Figure 3:
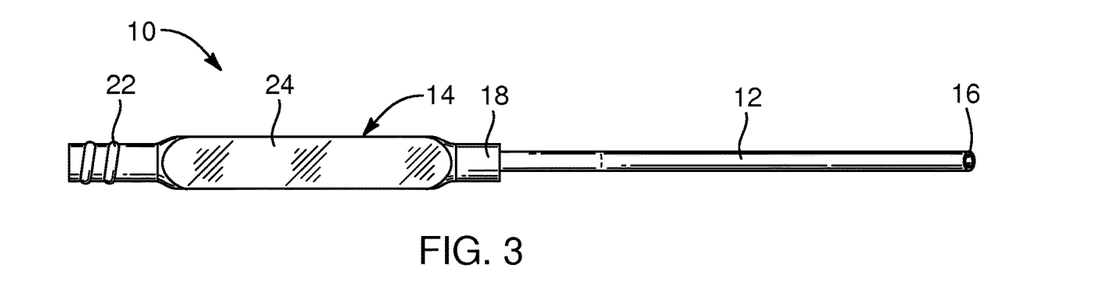
FIG. 3 is a bottom plan view thereof.
Figure 4:
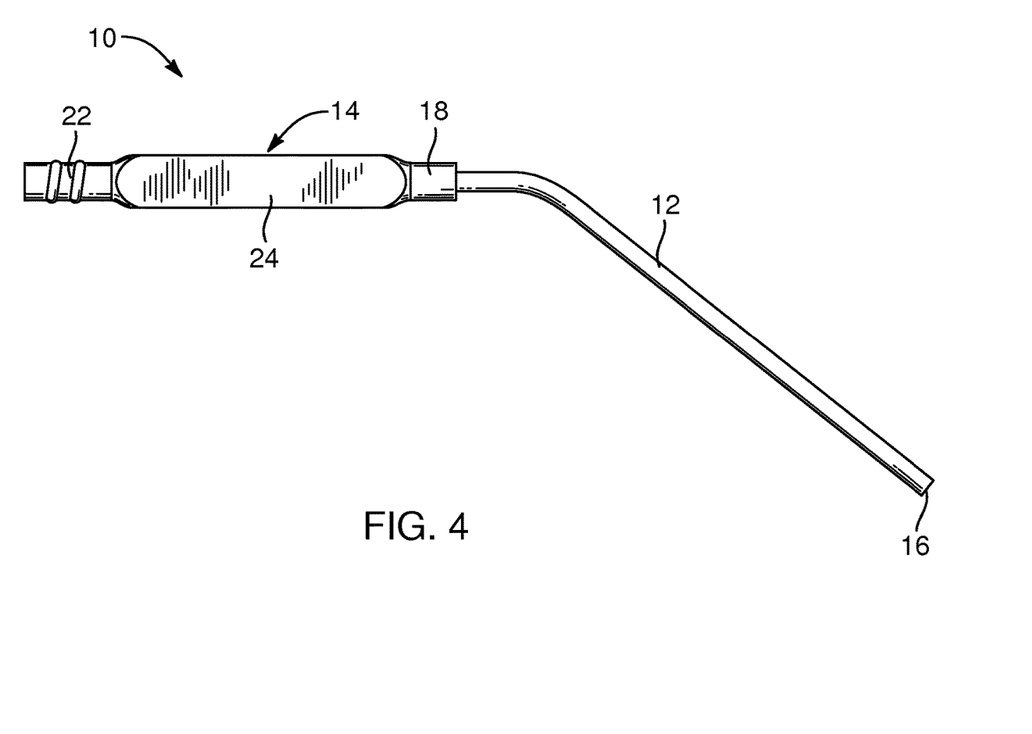
FIG. 4 is a right side elevation view thereof.
Figure 5:
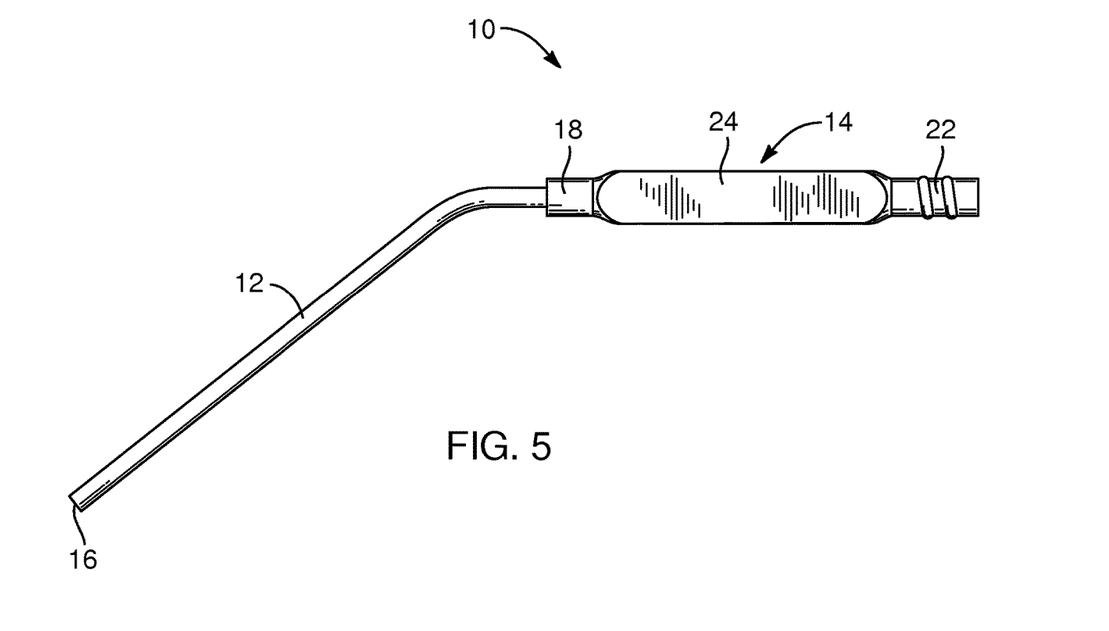
FIG. 5 is a left side elevation view thereof.
Figure 6:
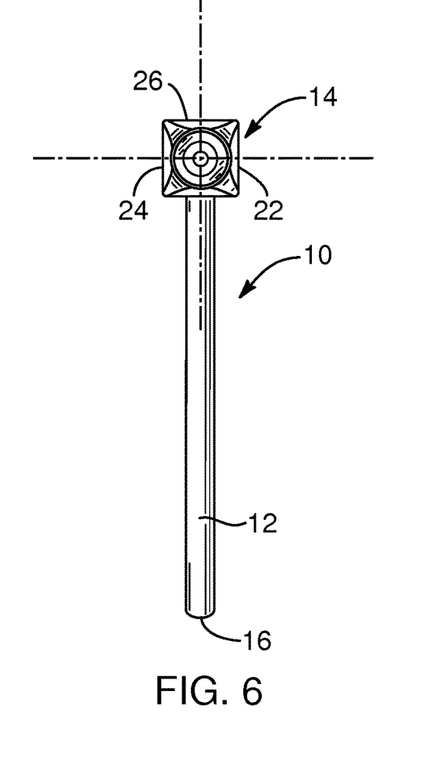
FIG. 6 is a back end elevation view thereof.
Figure 7:
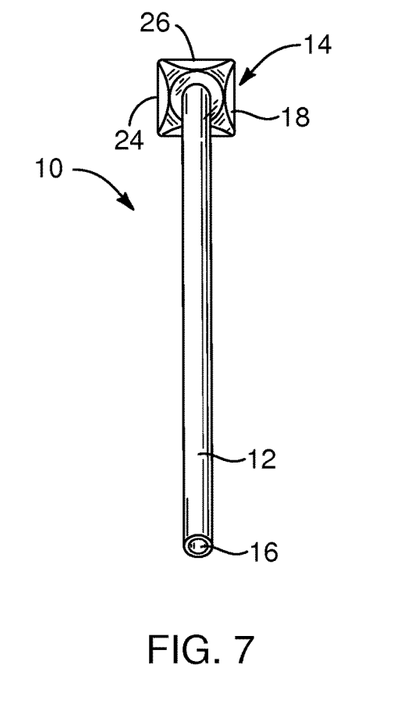
FIG. 7 is a front end elevation view thereof.

Referring to FIG. 1, while referring generally to FIGS. 1-13, a probe 10 or suction probe 10, may be thought of as a system 10 for introducing a probe 12 or tube 12 controllable by use of a handle 14. In general, the handle 14 may have multiple angles and surfaces to assist in manipulation.

The receiver 18 may be formed at one end of the handle 14 and is sized to provide a fit and stoppage orientation for the probe 12. For example, in one embodiment, the receiver 18 may be provided with a central bore that terminates at a shoulder. In this way, the probe 12 may be fitted into the channel or bore of the receiver 18, up to the point that the probe 12 stops against the shoulder. In certain embodiments, the receiver 18 may be sized for an interference fit with the probe 12. In fact, the probe 12 may be formed as a single, comparatively long, straight, tube 12. A core, such as a flexible plastic rod may be threaded through the entire length of the probe 12, and may actually remain visible at both ends of the probe 12, and the handle 14. In this way, a surgeon may actually curve, bend, or angle (without buckling) the probe 12. The probe may thus be formed at any suitable angle, or at multiple suitable angles in order to fit around particular obstructions, and arrive at the proper path, orientation, and location, with respect to the handle 14, for use.

Typically, the receiver 18 may have an interference fit with its internal bore against the outer surface of the probe 12, and may receive such in various ways. For example, the probe 12 may be heated and inserted hot into the receiver 18. In other embodiments, the receiver 18 and handle 14 may actually be molded around the probe 12, with the probe 12 acting as a mold insert 12. In other embodiments, the interference fit may be sufficiently tight that a mechanical force acting axially along the length of the probe 12, may secure the probe 12 in the receiver 18.

In certain embodiments, an aperture 20 may be provided, constituting a passage 20 from the outside environment into the interior of the handle 14. Typically, the aperture 20 will be positioned to identify and distinguish the sides 24 from the top 26 of the handle 14. For example, the sides 24 have no aperture 20. However, the top 26 or top surface 26 has the aperture 20 formed therein, and easily accessible.

Typically, the sides 24 and top 26 are at right angles or 90 degree angles with respect to one another in order to provide a firm grip for aiming, pointing, or otherwise positioning the probe 12, and specifically the end 16 or tip 16 thereof. Likewise, the location of the aperture 20 in the top surface 26 provides a designation of orientation.

Thus, to a certain extent, the probe 12 may be moved, even when not visible, with a degree of accuracy and predictability, due to the orientation of the aperture 20 indicating the location and orientation of the end 16 of the probe 12.

Typically, the end 16 of the probe 12 operates as the suctioning portion. An interface 22 at an opposite end of the handle 14 operates to connect to a pump or vacuum source. The interface 22 may be threaded, or simply have a fitting for securing to a hose, line, or the like drawing a continual flow, and thus supplying a reduced pressure or "vacuum" as it is conventionally called in lay terms.

Referring to FIGS. 1-7, while continuing to refer generally to FIGS. 1-13, the probe 12 may proceed from the receiver 18 a distance, after which the probe 12 angles down and away from the top 26. The rectangular cross-section along the axial direction of the handle 14 provides for an easy grip, particularly for rotating the probe 12 against the leverage advantage of the tip 16 or end 16 thereof. That is, the comparative length of the probe 12 provides substantial leverage advantage for the tip 16, to resist rotation of the handle 14 by a surgeon. Accordingly, the square or rectangular cross-section of the handle 14 provides certainty of grip, as well as a designation of the orientation of the probe 12 with respect to the handle 14.

Figure 8:
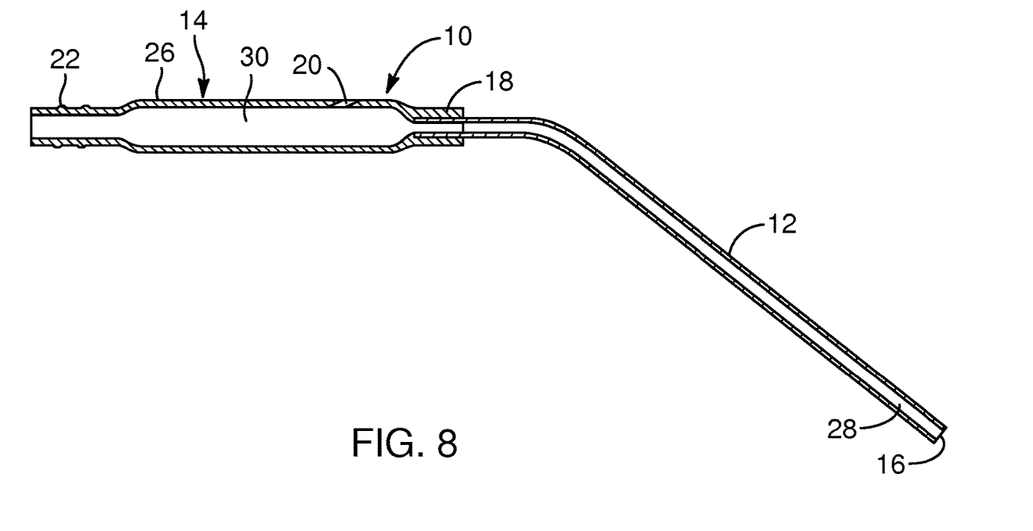
FIG. 8 is a right side, cross-sectional, elevation view thereof.

Referring to FIG. 8, while continuing to refer generally to FIGS. 1-13, a probe 12 may be hollow to provide a lumen 28 or channel 28 for drawing fluids through the probe 12 and the handle 14. Accordingly, a cavity 30 exists likewise in the handle 14. The cavity 30 may have a larger cross-sectional area, or larger effective diameter than that of the lumen 28 of the probe 12. In other embodiments, the cavity 30 may have a circular diameter identical to that of the probe 12.

Figures 9, 11:
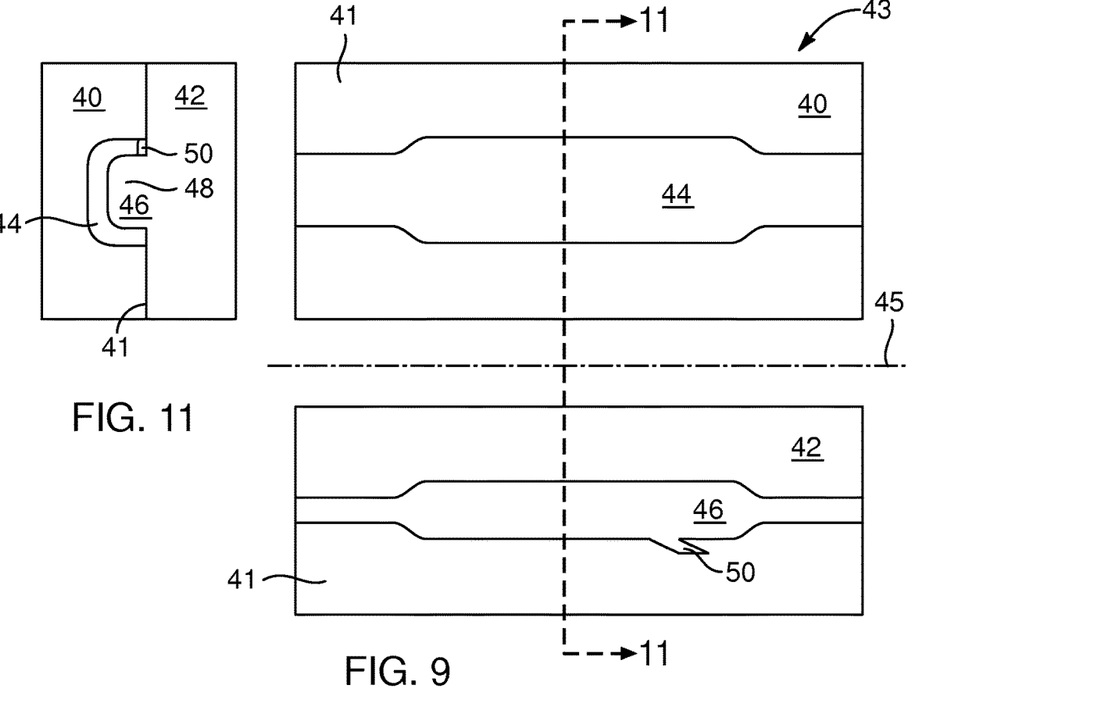
FIG. 9 is a right side elevation view of one embodiment of a mold showing a mold cavity therein, as the top rectangular image, and the matching, left side elevation view, opened up as if hinged, is illustrated.
FIG. 11 is an end elevation view, in cross-section, of the mold of FIG. 9.
Figure 10:
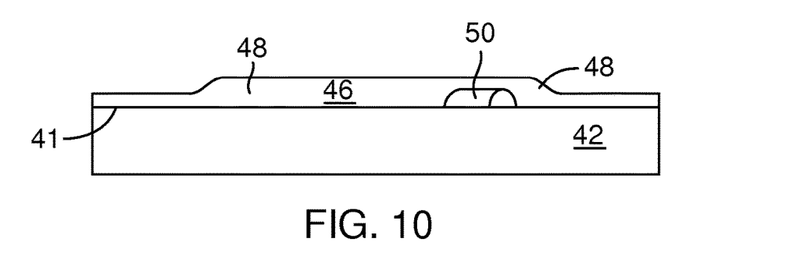
FIG. 10 is a top plan view of the right mold piece, showing its cord portion.

Referring to FIGS. 9-11, a mold for making a handle 14 in accordance with the invention may have two mold halves 40, 42 that assemble together or fold together along a parting surface 41 or parting line 41. In the illustrated embodiment, the mold 43 may have one mold half 40 that includes a cavity 44 shaped to the outer configuration of the handle 14.

Opposite the mold half 40 is a mold half 42 that includes a core 46 that will actually fit inside the cavity 44 of the mold half 40. One will note that the core 46 has a main portion 48 and a vent portion 50. The main portion 48 sweeps out the cavity 30, while the main cavity 44 of the mold half 40 receives a plastic, resin, or other material that will form the body of the handle 14.

The vent portion 50 actually contacts the surface of the cavity 44, thus providing the aperture 20 in the handle 14. In the illustrated embodiment, the mold halves 40, 42 assemble as illustrated in FIG. 11. The core 46, and particularly the main portion 48 extends into the cavity 44 to leave open only the portion of the cavity 44 that will receive material for the handle 14.

Meanwhile, the main portion 48 extends substantially into the cavity 44, to preclude filling that portion thereof with the polymeric resin, such as a suitable plastic material. Meanwhile, the vent portion 50 extends out up to contact the wall of the cavity 44, thus precluding any material from entering therein.

In the illustrated embodiment, a mirror-image of all components may be manufactured. For example, the cavity 44 molds a single half of the handle 14. The opposite half of the handle 14 may be fabricated by a mirror-image of this particular half. The half illustrated is the left half, and the mirror-image would be a right half. After release from the mold 43, each half of the handle 14 may then be assembled to its mirror-image half, and both be glued together.

In yet another alternative embodiment, the mold 43 may be formed to inject in two halves that separate end-to-end from one another. In such an embodiment, long lengths and the typical requirement for draft would typically cause a tapered shape for the handle 14. Thus, a mold in accordance with such an embodiment may actually form the entire handle 14 in a single, two-piece mold. However, such would require tapering of the outer surfaces 24, 26 of the handle 14, as well as the internal walls of the cavity 30. That is, draft requirements would require this. Meanwhile, the aperture 20 would require a core pull in order to leave a suitable passage 20 or aperture 20.

Figure 12:
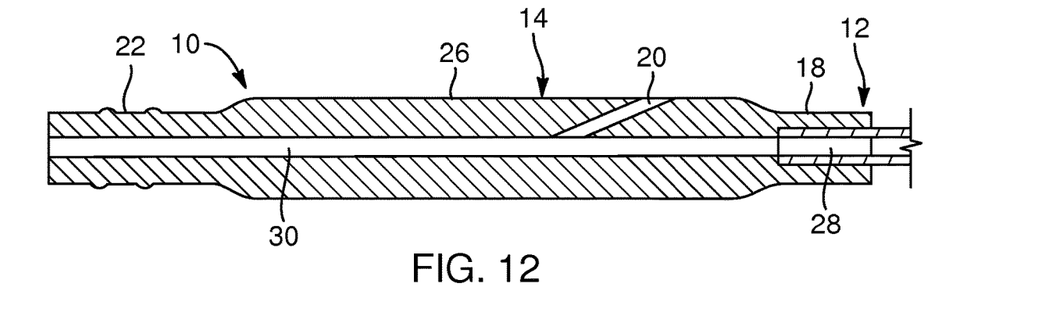
FIG. 12 is a side, elevation, cross-sectional view of a handle in accordance with the invention, manufactured in a single molding step.
Figure 13:
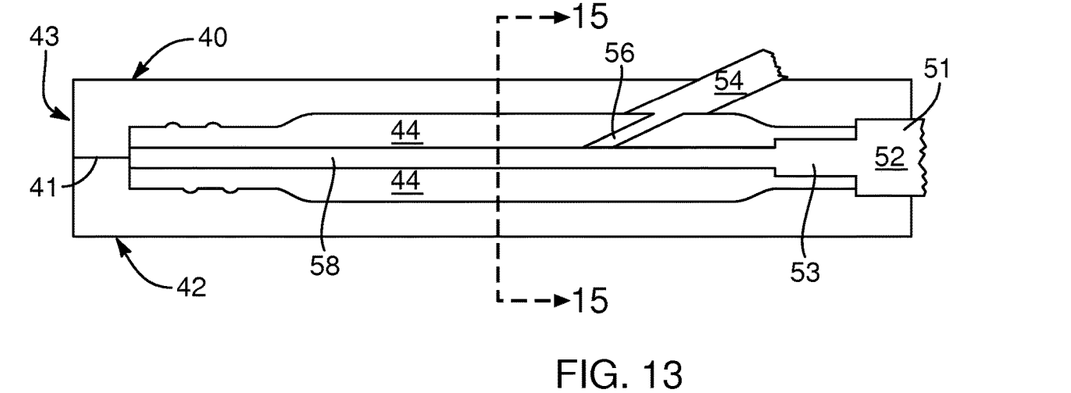
FIG. 13 is a side, elevation, cross-sectional view of a mold with cores for manufacturing the handle of FIG. 12.
Figure 14:
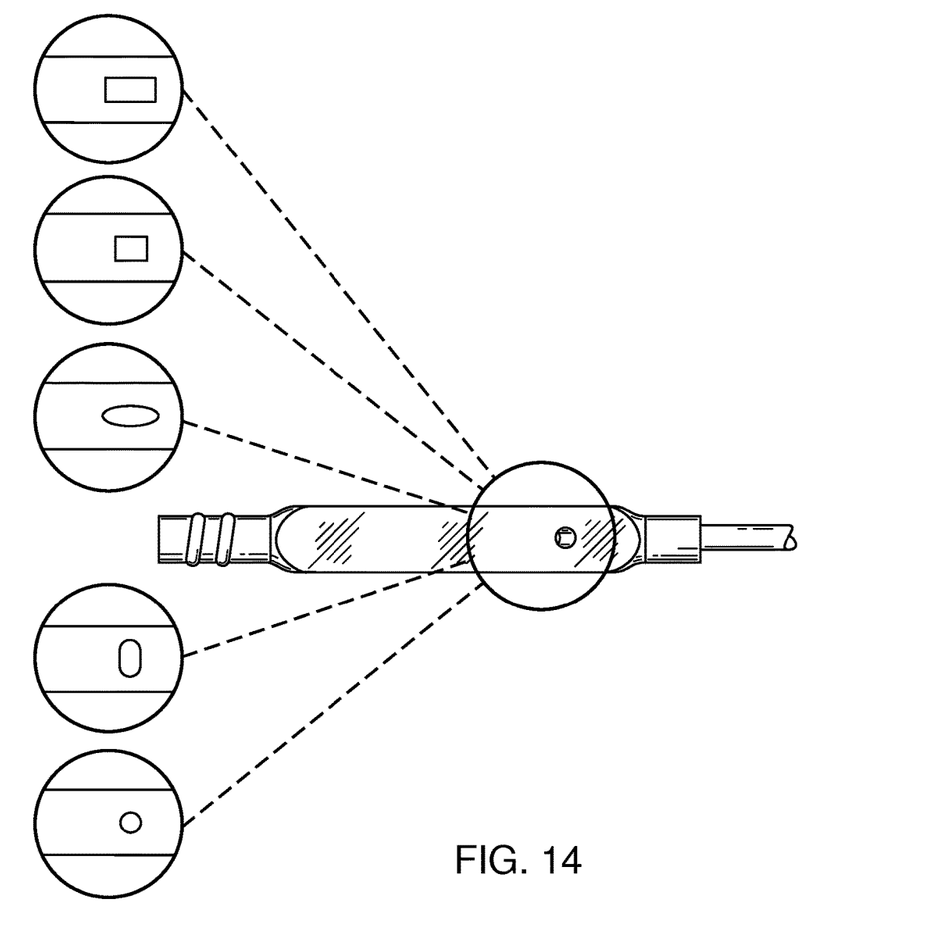
FIG. 14 is a top plan view of the handle, showing various, possible shapes for the aperture.
Figure 15:
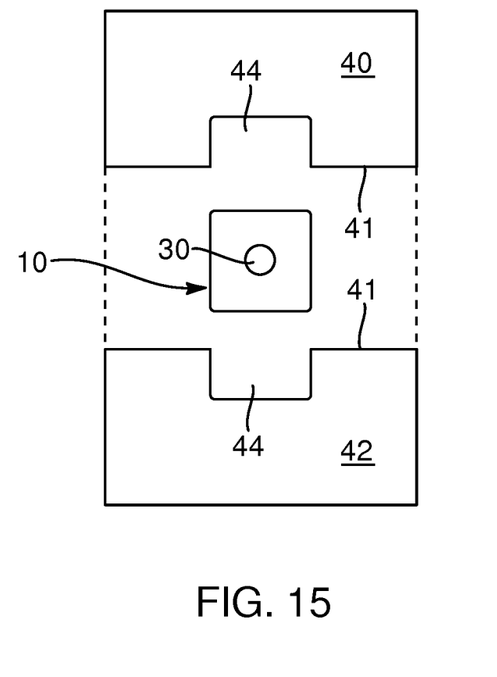
FIG. 15 is an end elevation view, in cross-section, of the mold of FIG. 13.

Referring to FIGS. 12-13, the handle 14 may be formed in a mold 43 of alternate design. For example, a mold 43 may have mold halves 40, 42, meeting at a parting line 41 or parting surface 41. In the illustrated embodiment, the handle 14 may be formed in a cavity 44. In the illustrated embodiment, the cavity 44 receives the resin that will cure to become the plastic of the handle 14. Typically, the cavity 30 will have suitable draft angles (be tapered) somewhat. However, it is sufficient if a mold release is used, and if all changes in cross-sectional area are monotonically decreasing from right to left in the illustrated embodiment. Similarly, monotonically decreasing sizes from left to right may also be used. However, interior changes in cross-section may be limited.

For example, in the illustrated embodiment, the shaft 51 may be a powered ram 51 that draws a central core 52 from the handle 14 after molding. The central core 52 may operate as a core pull, and may have changes in cross-section, such as the shoulder portion 53, that is smaller than the shaft 51, but larger than the central cavity portion 58.

In the illustrated embodiment, a vent core 54 may also draw out of the handle 14 in the cavity portion 44, prior to opening the mold 43 by separating the mold halves 40, 42 along the parting line 41 or surface 41. Typically, a vent pin portion 56 will be sized and shaped to actually contact the central cavity portion 58, in order to prevent flash or injection of any resin material there.

Thus, the image of FIG. 13 represents a cross-sectional view of the cavity of a mold 43 in its associated hardware required. Here, the configuration is that required for injection, all in a closed configuration. At this point, gated runners may feed into the cavity 44 the liquid resin that will harden or cure to become the handle 14.

Following cooling, which may require only a matter of seconds, the core 54 or vent core 54 must be withdrawn first. Thereafter, the core 52 may either be drawn, or may simply be removed, or even maintained in place while the core halves 40, 42 are separated. Ultimately, the core 52 must be withdrawn from the handle 14 remaining. Accordingly, it is typical that a core pull 54 or the core 54 is pulled, followed by pulling the core 52, followed by opening of the mold 43 by the separation of the mold halves 40, 42.

Thus, the vent pin portion 56 is responsible for leaving the aperture 20. The central cavity portion 58 of the core 52 is responsible for leaving the cavity 30 in the handle 14. The shoulder portion 53 of the core 52 is responsible for leaving the internal bore of the receiver 18, sized to receive the probe 12. In this embodiment, the internal cavity 30 extends into the interface 22 or connector 22, as formed.

In yet another alternative embodiment, the handle may be molded by any suitable means. The aperture may then be drilled.

The present invention may be embodied in other specific forms without departing from its purposes, functions, structures, or operational characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus formed as a suction tool capable of selective, intermittent activation exclusively between two conditions, an active suction condition and a bypass condition, exclusively by a user, during a surgical procedure requiring removal of liquid from an operating space, the apparatus comprising:
   a handle, having a cavity therewithin, the cavity defining a length, between an inlet and an outlet having a cross-sectional area orthogonal thereto, and being sized and shaped to be capable of whistling when subject to a disturbance from air admitted into the cavity other than through the inlet, the whistling having a characteristic consisting of at least one of volume and pitch effective to interfere with the procedure;
   a probe extending from the operating space into the inlet of the cavity to retrieve the liquid by becoming an exclusive path into the cavity when positioned to remove the liquid; and
   a vent, constituting a fixed and solitary aperture selectively providing an alternate path for air into the cavity and a blockage of all air against entry thereinto through the vent, the aperture being shaped and positioned to be capable of being selectively controlled directly and exclusively by contact of the aperture directly with a digit of a user participating in the procedure to thereby change functionality of the handle between, and consisting of, the active suction condition permitting passage of fluids only into the probe and out of the outlet, and the bypass condition permitting air to enter the cavity through the vent and render ineffective the active suction through the probe, the vent being sized, shaped, and located to effect reduction of the whistling sufficiently to cease interference with the procedure, wherein the vent remains within a single cross-sectional area perpendicular to a centerline thereof.

2. The apparatus of claim 1, wherein the vent impinges on the cavity at a single angle.

3. The apparatus of claim 2, wherein the probe is formed to provide a lumen therein maintaining fluid communication with the cavity.

4. The apparatus of claim 3, comprising a fitting shaped to receive a vacuum source drawing fluids through the probe, handle, and fitting in response to a complete occlusion of the vent by the hand of the user.

5. The apparatus of claim 1, comprising the vent, sized and shaped based on the cavity to eliminate the noise corresponding to a size and shape of the cavity, otherwise effective to whistle in response to air entering the cavity from other than the probe, effective to interfere with the procedure.

6. The apparatus of claim 1, wherein the cavity is capable of producing the whistling effective to interfere with the procedure if characterized by a single angle selected to be more toward perpendicularity with the length.

7. The apparatus of claim 1, wherein the vent is angled into the cavity at from 30 degrees to 70 degrees.

8. An apparatus operable as a suction tool in a surgical procedure, being capable of selective, intermittent, operation, exclusively by a user and exclusively between two conditions, a suctioning condition capable of passing fluid therethrough exclusively along a first path fixed in the apparatus, and a bypass condition capable of flowing fluid through the first path and a second path, fixed within the apparatus, the apparatus comprising:
   a handle, having a cavity therewithin defining a length between an inlet thereto and an outlet therefrom and a cross-section orthogonal to the length;

the handle, having a size and shape corresponding to a whistling in response to a disturbance of air admitted into the cavity from other than the inlet, the whistling characterized by a combination of volume and pitch effective to interfere with the procedure;

the handle having a flat side extending parallel to the length;

a probe extending from the operating space into the inlet of the cavity to retrieve the liquid by becoming an exclusive path into the cavity when positioned to remove the liquid; and a vent, penetrating into the cavity from the flat side of the handle to be accessible to and operable by a thumb and by a finger of a hand of a user, the vent constituting a solitary aperture as the exclusive second path, wherein the vent remains within a single cross-sectional area along a centerline therethrough.

9. The apparatus of claim 8 wherein the vent is shaped and positioned to be capable of being controlled directly and exclusively by contact between the aperture and skin of a user participating in the procedure to thereby switch the condition of the apparatus and remediate the whistling sufficiently to cease interference with the procedure.

10. An apparatus operable as a suction tool in a surgical procedure, being capable of selective, intermittent, operation, exclusively by a user and exclusively between two conditions, a suctioning condition capable of passing fluid exclusively along a first path predetermined through the apparatus, and a bypass condition capable of flowing fluid through the first path and a second path, predetermined through the apparatus, the apparatus comprising:

a handle, having a cavity therewithin defining a length between an inlet thereto and an outlet therefrom and a cross-section orthogonal to the length;

the handle, having a size and shape corresponding to a whistling in response to a disturbance of air if admitted into the cavity from other than the inlet, the whistling characterized by a combination of volume and pitch effective to interfere with the procedure;

the handle having a flat side extending parallel to the length; and a vent, penetrating into the cavity from the flat side of the handle to be accessible to and operable by a thumb and by a finger of a hand of a user, the vent constituting a solitary aperture as the exclusive second path, wherein the vent remains within a single cross-sectional area along a centerline of the vent .

11. The apparatus of claim 10 wherein the vent is shaped and positioned to be capable of being controlled directly and exclusively by contact between the aperture and skin of a user participating in the procedure to thereby switch the condition of the apparatus and remediate the whistling sufficiently to cease interference with the procedure.

12. The apparatus of claim 10, wherein the vent is constituted by a wall entirely formed by the handle, and a single entry, fixed in area and selectively sealable by skin of the user.

* * * * *